(12) United States Patent
Kang

(10) Patent No.: US 8,899,747 B2
(45) Date of Patent: Dec. 2, 2014

(54) STEREOVISION OPTOMETRY APPARATUS

(71) Applicant: Catholic University Industry Academic Cooperation Foundation, Seoul (KR)

(72) Inventor: Hang-Bong Kang, Seoul (KE)

(73) Assignee: Catholic Univ. Ind. Academic Cooperation Found., Seoul (KR)

( * ) Notice: Subject to any disclaimer, the term of this patent is extended or adjusted under 35 U.S.C. 154(b) by 65 days.

(21) Appl. No.: 13/852,721

(22) Filed: Mar. 28, 2013

(65) Prior Publication Data

US 2014/0211153 A1 Jul. 31, 2014

(30) Foreign Application Priority Data

Jan. 28, 2013 (KR) ........................ 10-2013-0009063

(51) Int. Cl.
*A61B 3/08* (2006.01)
*H04N 13/04* (2006.01)
*A61B 3/02* (2006.01)
*A61B 3/09* (2006.01)

(52) U.S. Cl.
CPC ... *A61B 3/08* (2013.01); *A61B 3/02* (2013.01); *H04N 13/0443* (2013.01); *A61B 3/09* (2013.01)
USPC ........... 351/201; 351/202; 351/203; 351/222; 351/223; 359/466; 359/471; 359/472; 359/475; 359/476; 359/477

(58) Field of Classification Search
CPC ............ H04N 13/004; H04N 13/0443; H04N 13/0447; H04N 13/0452; A61B 3/02; A61B 3/08; A61B 3/085
USPC .................. 348/E13.029; 351/201, 202, 203; 382/154
See application file for complete search history.

(56) References Cited

U.S. PATENT DOCUMENTS

| | | | | |
|---|---|---|---|---|
| 5,099,858 | A | * | 3/1992 | Hofeldt ........................ 600/558 |
| 5,270,751 | A | * | 12/1993 | Christian .......................... 353/7 |
| 5,530,492 | A | * | 6/1996 | Ron .............................. 351/201 |
| 5,644,427 | A | * | 7/1997 | Omori et al. .................. 359/464 |
| 5,682,171 | A | * | 10/1997 | Yokoi ............................... 345/7 |
| 5,712,732 | A | * | 1/1998 | Street ............................ 359/630 |
| 5,726,800 | A | * | 3/1998 | Ezra et al. ..................... 359/466 |
| 5,886,818 | A | * | 3/1999 | Summer et al. ................ 359/478 |
| 5,912,650 | A | * | 6/1999 | Carollo ............................ 345/7 |
| 5,933,210 | A | * | 8/1999 | Ron .............................. 351/246 |
| 6,011,580 | A | * | 1/2000 | Hattori et al. ................... 348/57 |
| 6,014,164 | A | * | 1/2000 | Woodgate et al. .............. 348/51 |
| 6,042,235 | A | * | 3/2000 | Machtig et al. ................ 353/28 |

(Continued)

*Primary Examiner* — William Choi
*Assistant Examiner* — Collin X Beatty
(74) *Attorney, Agent, or Firm* — North Weber & Baugh LLP

(57) ABSTRACT

The invention relates to a stereovision optometry apparatus comprising: a 3D display unit for displaying 3D image; a reference 2D display unit for displaying reference 2D image; an eyepiece in opposite side of the 2D display unit configured to view the images; a reflective mirror in opposite side of the 3D display unit configured to move toward and away from the 3D display unit; and a half mirror arranged between the 3D display and the reflective mirror and disposed at a point where propagation paths of the 2D image and the 3D image intersect; wherein the 2D image penetrates through the half mirror to reach the eyepiece; wherein the 3D image penetrates the half mirror to be reflected on the reflective mirror and then the reflected image is reflected on the half mirror to reach the eyepiece.

10 Claims, 9 Drawing Sheets

(56) References Cited

U.S. PATENT DOCUMENTS

| | | | |
|---|---|---|---|
| 6,054,969 A * | 4/2000 | Haisma | 345/7 |
| 6,061,489 A * | 5/2000 | Ezra et al. | 385/115 |
| 6,124,920 A * | 9/2000 | Moseley et al. | 349/201 |
| 6,525,699 B1 * | 2/2003 | Suyama et al. | 345/6 |
| 6,542,297 B1 * | 4/2003 | Lee et al. | 359/466 |
| 6,611,243 B1 * | 8/2003 | Moseley et al. | 345/4 |
| 6,703,988 B1 * | 3/2004 | Fergason | 345/6 |
| 6,886,940 B2 * | 5/2005 | Liang et al. | 353/7 |
| 7,144,113 B2 * | 12/2006 | Fujikawa et al. | 353/7 |
| 7,414,831 B1 * | 8/2008 | Brown et al. | 361/679.27 |
| 7,538,876 B2 * | 5/2009 | Hewitt et al. | 356/364 |
| 7,719,770 B2 * | 5/2010 | Jang | 359/633 |
| 8,066,382 B2 * | 11/2011 | Silverstein et al. | 353/20 |
| 8,125,583 B2 * | 2/2012 | Hayashi et al. | 349/15 |
| 8,243,125 B2 * | 8/2012 | Tomisawa et al. | 348/51 |
| 8,279,271 B2 * | 10/2012 | Choi | 348/58 |
| 8,355,094 B2 * | 1/2013 | Nittou | 349/62 |
| 8,384,769 B1 * | 2/2013 | Hong et al. | 348/51 |
| 8,643,677 B2 * | 2/2014 | Suzuki | 345/635 |
| 2011/0267577 A1 * | 11/2011 | Verma | 351/201 |
| 2011/0304818 A1 * | 12/2011 | Reichow et al. | 351/201 |
| 2012/0002163 A1 * | 1/2012 | Neal | 351/201 |
| 2012/0050505 A1 * | 3/2012 | Yabui et al. | 348/54 |
| 2012/0249951 A1 * | 10/2012 | Hirayama | 351/201 |
| 2012/0307203 A1 * | 12/2012 | Vendel et al. | 351/201 |
| 2013/0044290 A1 * | 2/2013 | Kawamura | 351/201 |

* cited by examiner

US 8,899,747 B2

STEREOVISION OPTOMETRY APPARATUS

CROSS REFERENCE TO RELATED APPLICATIONS

The application claims the benefit of Korean Application Serial No. 10 2013 0009063, entitled "Stereovision Optometry Apparatus", filed on Jan. 28, 2013, the subject matter of which is incorporated herein by reference.

BACKGROUND

A. Technical Field

The present invention relates to a stereovision optometry apparatus and in particular to a stereovision optometry apparatus to check an individual stereovision condition.

B. Background of the Invention

Stereovision is one of the most important factors when 3D content is perceived. Stereovision is a phenomenon in which two images are combined into one image to provide a three-dimensional perception when two images for a particular object are viewed in such a manner one left eye takes a view of a left image and the other right eye takes a view of a right image at a visual range (approximately 25 cm).

Recently, 3D content is in high demand as 3D movies or 3D display devices such as 3D TV emerge. However, statistics show that about 15% of the population do not perceive or enjoy the three-dimensional effect.

Stereovision optometry apparatus or other device for 3D content which is being used or sold is able to detect only the presence of stereovision, not a degree in which an individual perceives, i.e., a degree in which an individual perceives content in three-dimensional.

SUMMARY OF THE INVENTION

An object of the present invention is to solve the above problems and to provide a stereovision optometry apparatus to determine an individual perception of stereovision accurately and precisely.

An object of the present invention is to solve the above problems and to provide a stereovision optometry apparatus to determine an individual perception of stereovision accurately and precisely.

An object of the present invention is to solve the above problems and to provide a stereovision optometry apparatus to determine an individual perception of stereovision accurately and precisely.

An object of the present invention is to solve the above problems and to provide a stereovision optometry apparatus to determine an individual perception of stereovision accurately and precisely.

According to the invention, a stereovision optometry apparatus to determine an individual perception of stereovision accurately and precisely is provided.

Therefore, the invention can be applied to examine ophthalmic diseases according to stereovision perception. In case of a 3D display apparatus such as 3D TV, reference information about 3D image suitable for each viewer can be provided to each viewer, thereby a 3D display apparatus which controls a protrusion angle is implemented.

BRIEF DESCRIPTION OF THE DRAWINGS

Further advantages of the invention are described in the following exemplary embodiments. There is showing.

DETAILED DESCRIPTION OF THE PREFERRED EMBODIMENTS

Hereinafter, preferred embodiments will be explained in detail referring to attached drawings.

Figure 1:
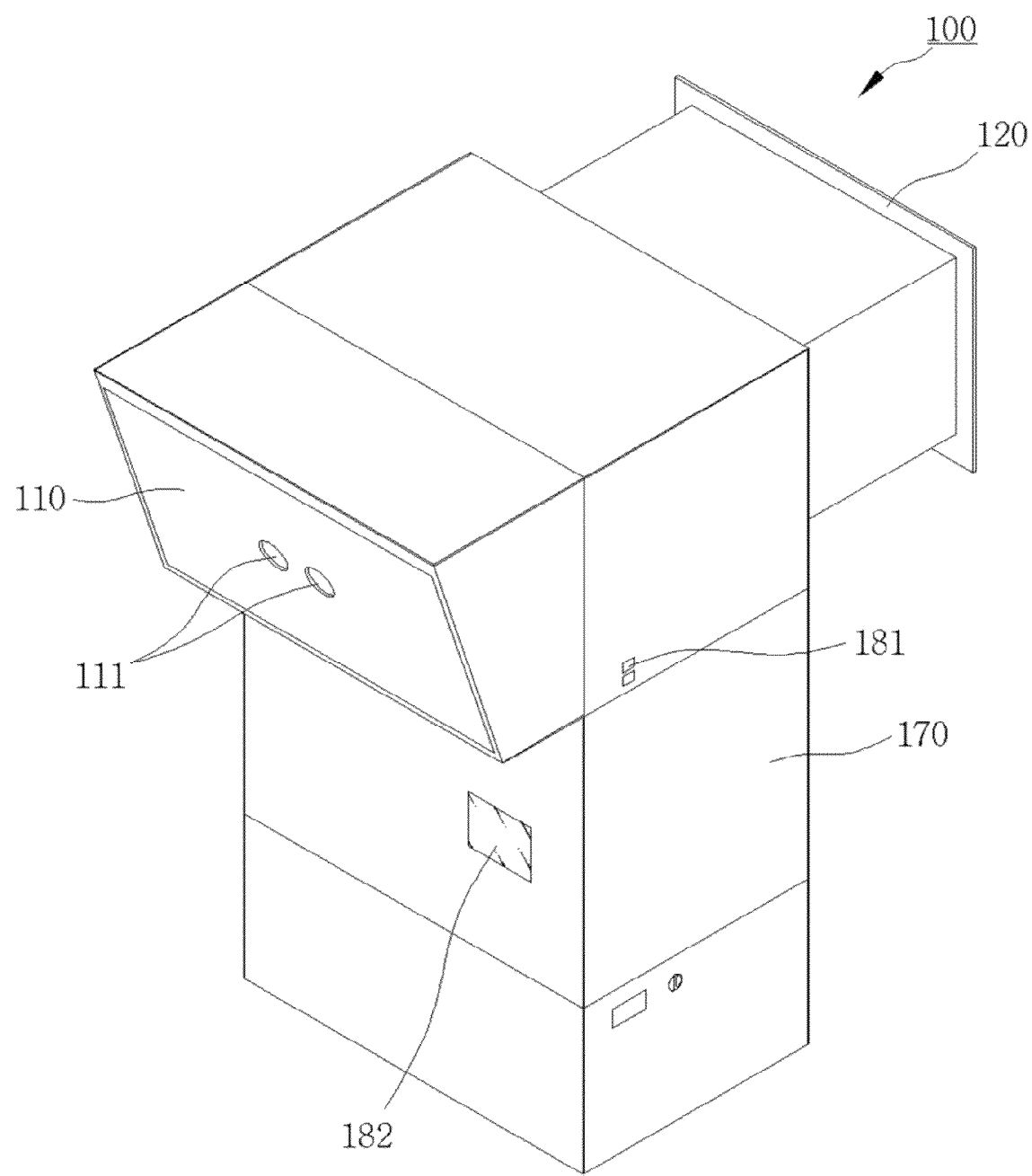
FIG. 1 is a perspective view of a stereovision optometry apparatus according to the invention.
Figure 2:
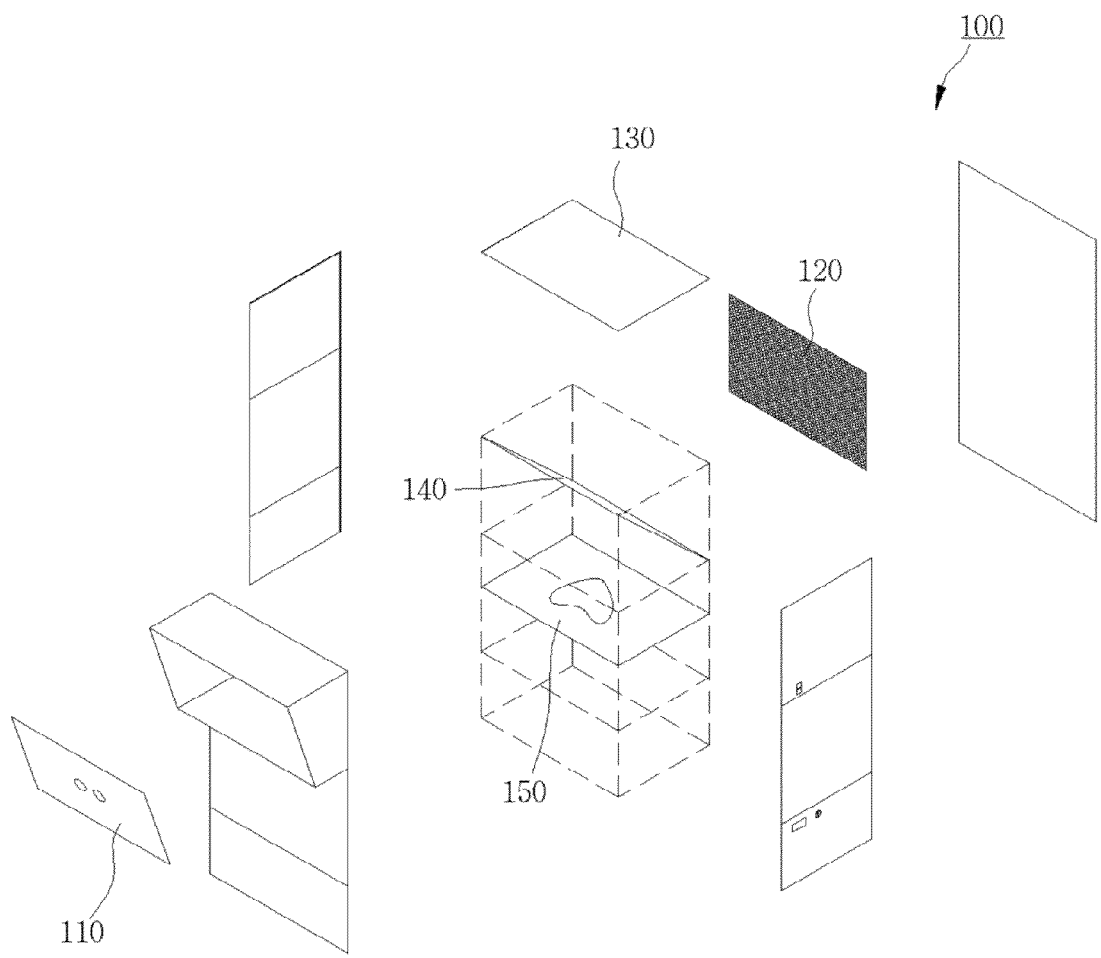
FIG. 2 represents schematically an exploded perspective view of a stereovision optometry apparatus according to the invention.
Figure 3:
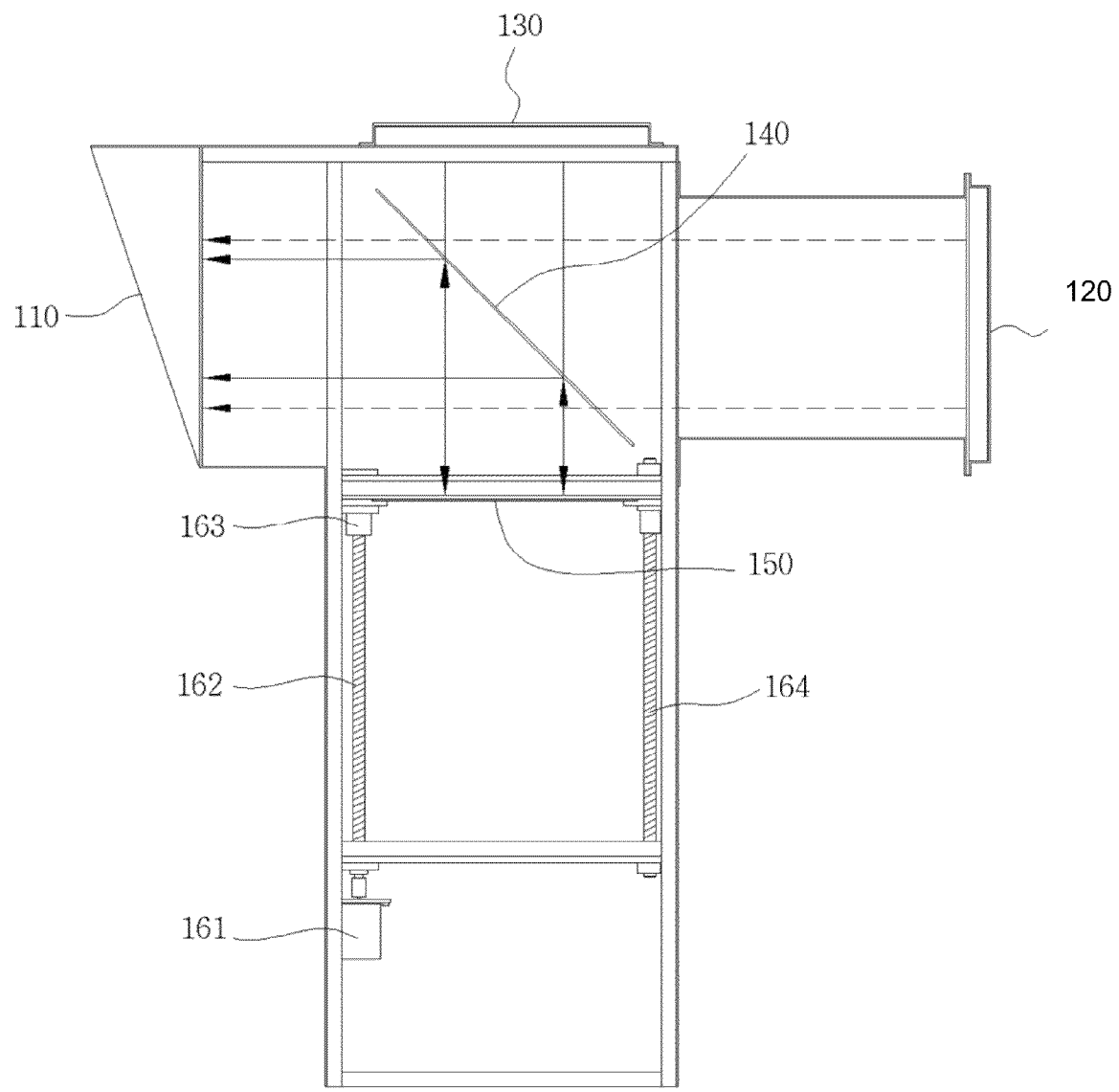
FIGS. 3 and 4 represent a cross-sectional view of a stereovision optometry apparatus according to the invention.
Figure 4:
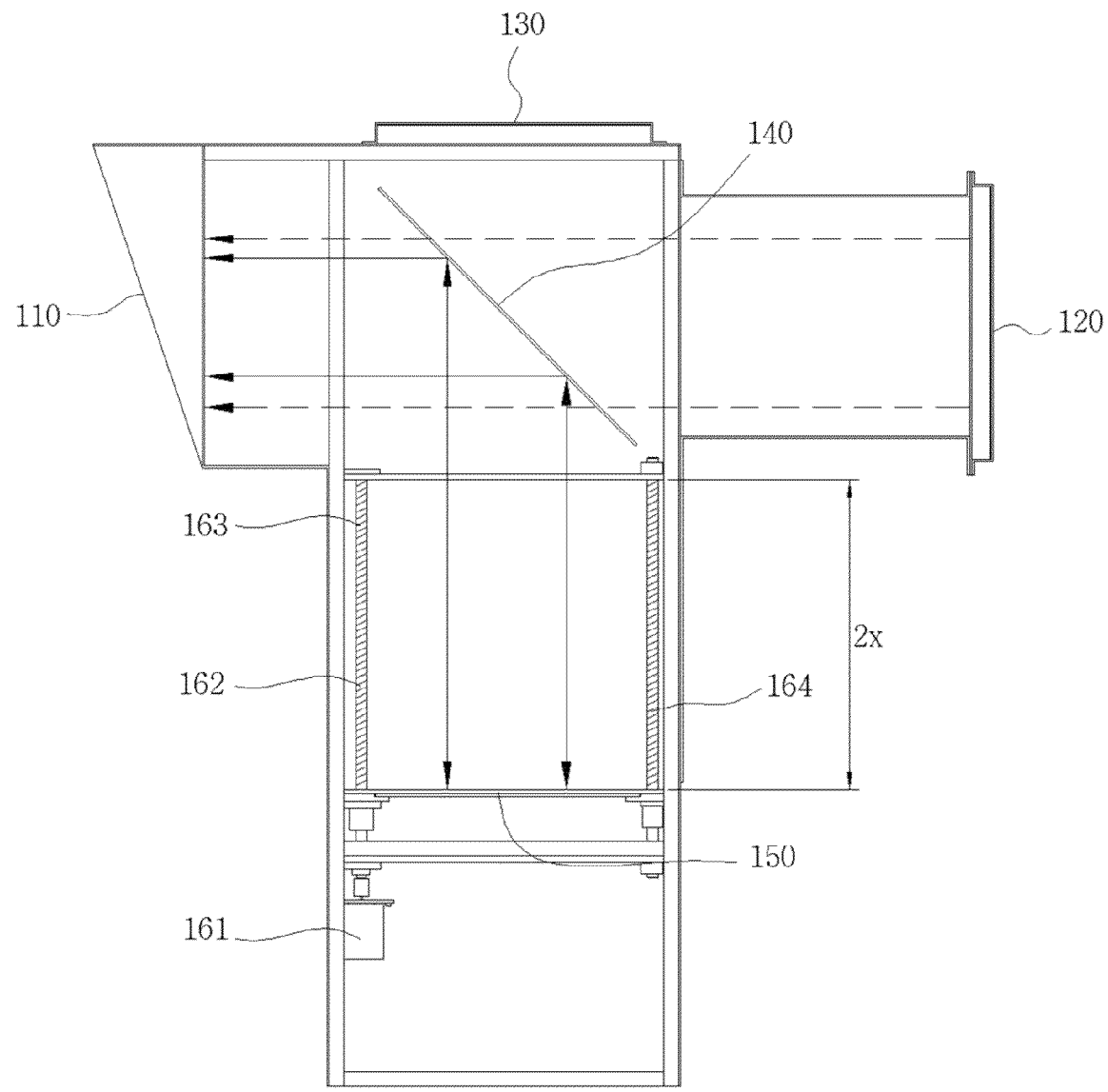

FIG. 1 shows a perspective view of a stereovision optometry apparatus 100 according to the invention, FIG. 2 represents schematically an exploded perspective view of a stereovision optometry apparatus 100 according to the invention, and FIGS. 3 and 4 represent a cross-sectional view of a stereovision optometry apparatus 100 according to the invention.

As shown in FIGS. 1 to 4, the stereovision optometry apparatus 100 comprises a 3D display unit 130, a reference 2D display unit 120, an eyepiece 110, a reflective mirror 150 and a half mirror 140. Here, the elements of the stereovision optometry apparatus 100 such as a 3D display unit 130, a reference 2D display unit 120, an eyepiece 110, a reflective mirror 150, a half mirror 140, etc. are received in a frame body 170 and/or mounted on a frame body 170, as shown in FIG. 1, thereby providing an assembly of the stereovision optometry apparatus.

The 3D display unit 130 displays a 3D image. In one example of the present invention, as shown in FIGS. 2 to 4, the 3D display unit 130 is provided on the top of the frame body 170 and then displays a 3D image downwardly.

The reference 2D display unit 120 displays a reference 2D image. In one example of the invention, as shown in FIGS. 3 and 4, the reference 2D display unit 120 is arranged in opposite side of the eyepiece 110 and displays a reference 2D image in a direction from the right to the left in FIGS. 3 and 4 while the 3D display unit displays a 3D image in a direction from the top to the bottom.

Therefore, the reference 2D image from the reference 2D display unit 120 and the 3D image from the 3D display unit intersect and the half mirror 140 is arranged at the point where the two images intersect as shown in FIGS. 3 and 4.

The eyepiece 110 is installed on the frame body 170 in such a manner that it is arranged in opposite side of the reference 2D display unit 120. Here, a viewer watches a reference 2D image from the reference 2D display unit 120 and a 3D image from the 3D display unit by means of two view holes 111 formed in the eyepiece 110. Also, a polarizing lens to watch a 3D image may be arranged in the view holes 111.

As shown in FIGS. 3 and 4, the reflective mirror 150 is arranged in opposite side of the 3D display unit 130 unit to reflect a 3D image displayed from the 3D display unit 130. Here, the reflective mirror 150 is installed on the frame body 170 in such a manner that it moves towards and/or away from the 3D display unit 130, in particular travels back and forth in an upward and/or downward direction in FIGS. 3 and 4.

The half mirror 140 is disposed between the 3D display unit 130 and the reflective mirror 150 and is arranged in the frame body 170 in such a manner that it is disposed in the area where a propagation path of the reference 2D image and a propagation path of the 3D image intersect as described above.

Referring to FIGS. 3 and 4, the propagation path of the reference 2D image from the reference 2D display unit 120 and the propagation path of the 3D image from the 3D display unit 130 will be described hereinafter.

The propagation path of the reference 2D image is represented by dotted lines in FIGS. 3 and 4, and the reference 2D image from the reference 2D display unit 120 penetrates through the half mirror 140 to reach the eyepiece 110.

The continuous lines in FIGS. 3 and 4 represent the propagation path of the 3D image and the 3D image from the 3D display unit 130 penetrates the half mirror 140 to reach the reflective mirror 150. Then, the 3D image which reflected on the reflective mirror 150 goes back to the half mirror 140 and then reflects toward the eyepiece 110 on the half mirror 140 to reach the eyepiece 110.

The propagation path of the 3D image from the 3D display unit 130 and the propagation path of the reference 2D image from the reference 2D display unit 120 respectively are arranged in such a manner that they cross at right angles and the half mirror 140 is arranged in such a manner that it has an inclination of 45° with respect to the propagation path of the reference 2D image and the propagation path of the 3D image.

As such, user is able to watch the 3D image and the reference 2D image simultaneously through the eyepiece 110 and a three-dimensional effect varies according to the movement of the reflective mirror 150 toward and/or away from the 3D display unit, i.e., according to the upward and downward movement of the reflective mirror, which will be described in detail below.

The reflective mirror 150 moves toward and/or away from the 3D display unit 130 along the propagation path of the 3D image by the actuation of mirror-movement means 161, 162, 163, 164 for moving the reflective mirror. The mirror-movement means 161, 162, 163, 164 are operated by the use of a ball screw and may comprise a ball screw 162, a ball nut 163, and a driving motor 161 as shown in FIGS. 3 and 4.

The ball screw 162 is arranged along the movement of the reflective mirror 150 toward and/or away from the 3D display unit, i.e., along the upward and/or downward direction in FIGS. 3 and 4. The ball nut 163 moves back and forth by the rotation of the ball screw 162 to make the reflective mirror 150 move toward and/or away from the 3D display unit 130. The driving motor 161 rotates the ball screw 162 in a normal direction and/or a reverse direction so that the ball nut 163 makes the reflective mirror 150 move toward and/or away from the 3D display unit 130.

The mirror-movement means 161, 162, 163, 164 comprise at least one guide bar 164 which is arranged along the moving direction of the reflective mirror 150 to guide the reflective mirror 150 toward or away from the 3D display unit.

The reflective mirror 150 is provided with a plurality of through-holes into which the ball screw 162 and the guide bar 164 penetrate so that the reflective mirror 150 moves back and forth. The through-holes are formed on the edges of the reflective mirror 150 to prevent them from affecting the 3D image reflected from the reflective mirror 150.

Hereinafter, the method for checking an individual stereovision condition using the stereovision optometry apparatus according to the invention will be described in detail.

FIG. 3 shows that the reflective mirror 150 is located closest to the 3D display unit 130 and FIG. 4 shows that the reflective mirror 150 is farthest from the 3D display unit 130. The reflective mirror 150 is arranged to move back and forth between the position closest to the 3D display unit and the position farthest from the 3D display unit.

Here, when the reflective mirror 150 is located closest to the 3D display unit 130, the reflective mirror is arranged in such a manner that the length of the propagation path of the 3D image from the 3D display unit to the eyepiece 110 is the same as the length of the propagation path of the reference 2D image from the reference 2D display unit to the eyepiece 110.

Figure 5:
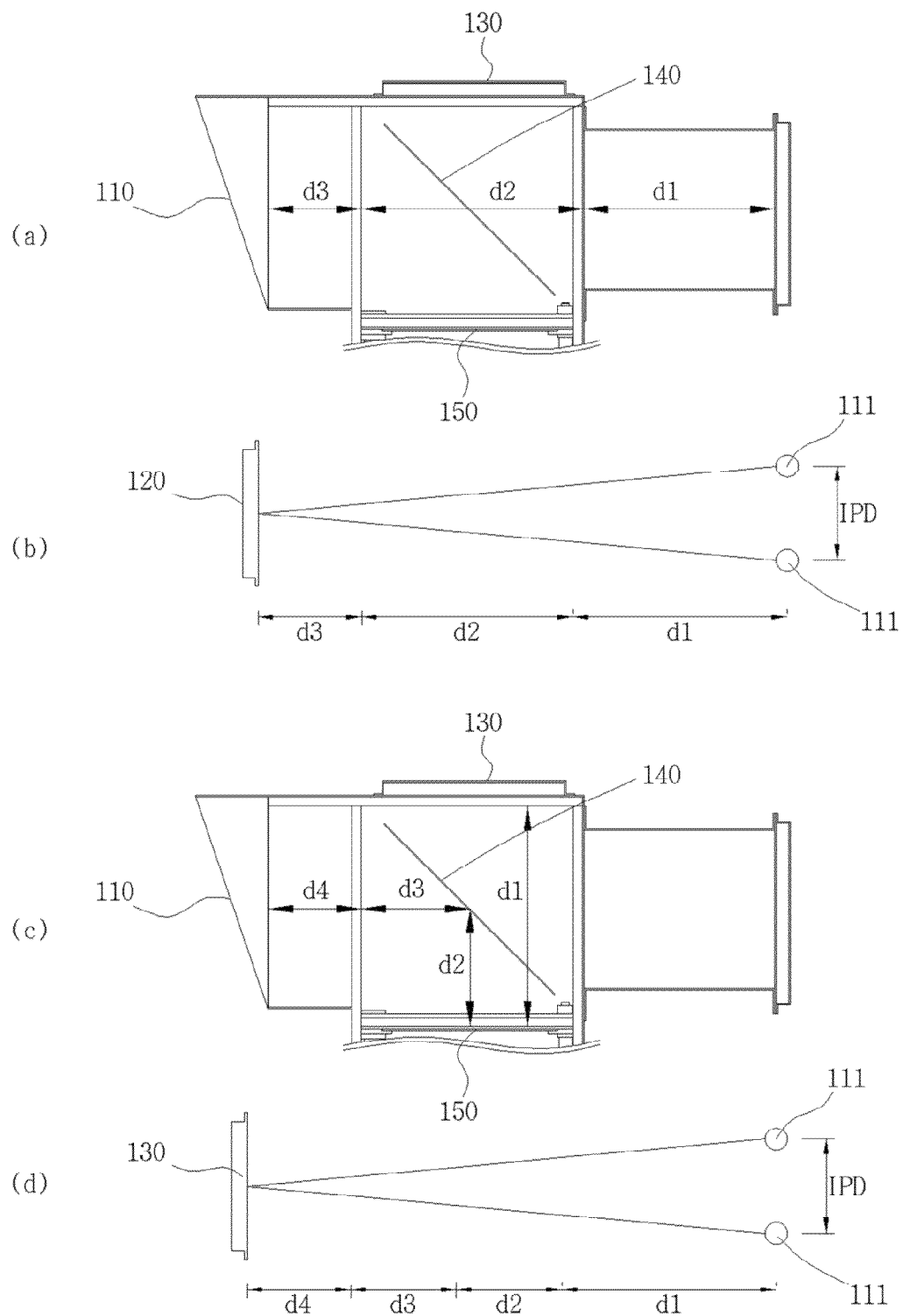
FIGS. 5 and 6 explain an operation principle of a stereovision optometry apparatus according to the invention.

Referring to FIG. 5, the total length d1+d2+d3 which is the sum of the propagation paths of the reference 2D image from the reference 2D display unit 120 as shown in FIGS. 5(a) and 5(b) is the same as the total length d1+d2+d3+d4 which is the sum of the propagation paths of the 3D image from the 3D display unit 130 as shown in FIGS. 5(c) and 5(d).

Then, when the reflective mirror 150 moves away from the 3D display unit 130 by the actuation of mirror-movement means 161, 162, 163, 164, the propagation length of the 3D image becomes longer than that of the reference 2D image.

Figure 6:
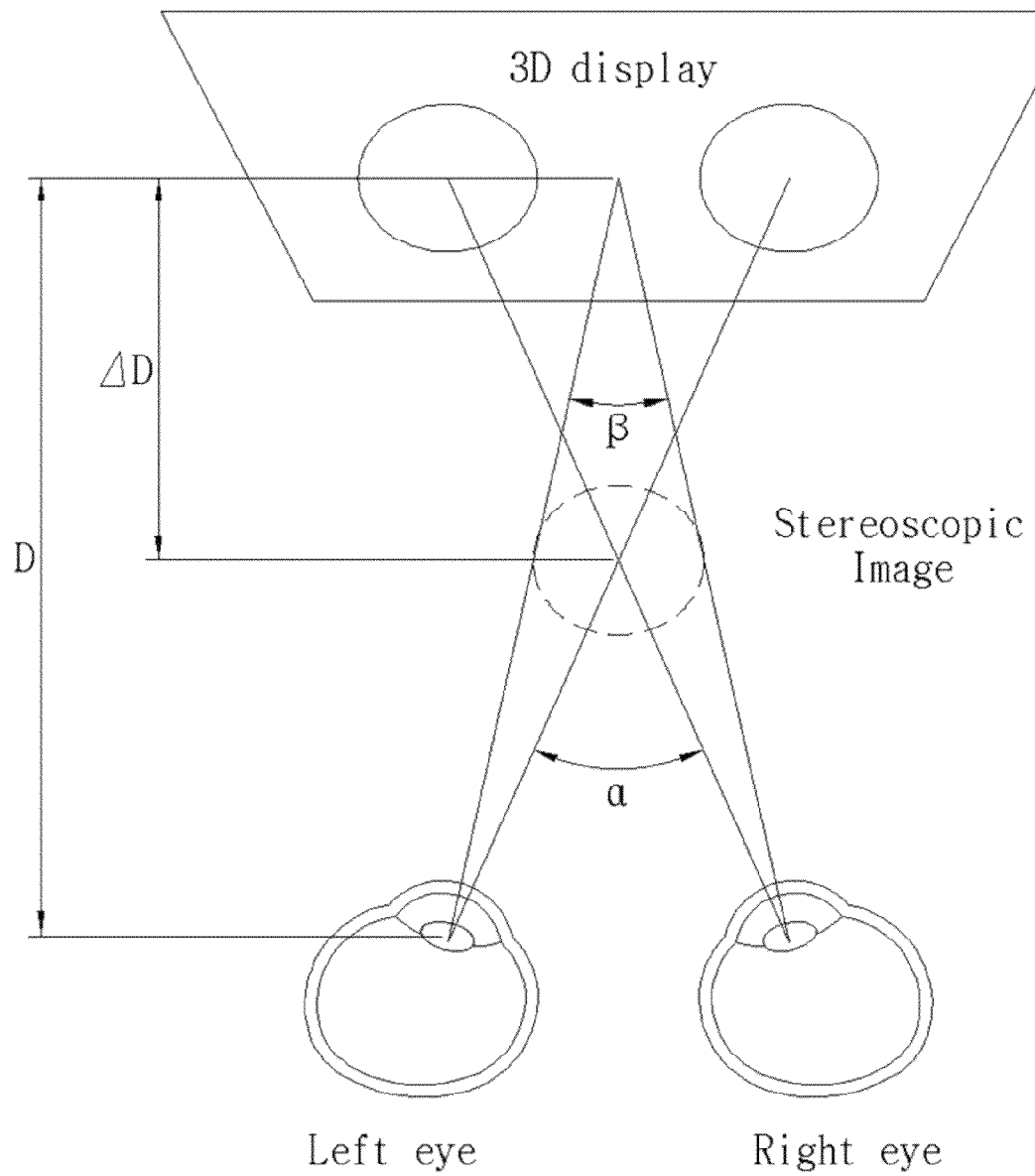

FIG. 6 explains an operation principle of a stereovision optometry apparatus according to the invention. As shown in FIG. 6, when a viewer watches 3D content such as 3D movie, convergence and accommodation occur simultaneously. Convergence refers to the combination of two 2D images into one 3D image and accommodation refers to the movement of focus.

In a natural viewing condition, eyes focus on the screen. Here, the difference between a convergence angle α and an accommodation angle β is referred to as a protrusion angle η and ΔD in FIG. 6 is referred to as a protrusion distance.

The stereovision optometry apparatus 100 according to the invention is provided to identify an error or a deviation between the theoretical degree of the protrusion, i.e., the protrusion angle and the protrusion distance, and the degree of protrusion experienced by a viewer and to find the degree of an individual's perception of stereovision.

In case that the length of the propagation path of the 3D image is the same as the length of the propagation path of the reference 2D image as shown in FIG. 3, when a viewer watches the reference 2D image and the 3D image through the eyepiece 110, the viewer feels that the 3D image is protruded more than the reference 2D image.

When the reflective mirror 150 moves downward, the protrusion degree of the 3D image, i.e., the depth of the 3D image varies and then a viewer finds a point where the reference 2D image is identical to the 3D image. As shown in FIG. 6, if α becomes the same as β by increasing the distance D between viewer's eyes and the 3D image, e.g., when the reflective mirror is located at a distance of "2×" in FIG. 4, a viewer will feel that the protrusion angle η and the protrusion distance ΔD become 0 and the distance thereof will be a protrusion distance which a viewer perceives.

Figure 7:
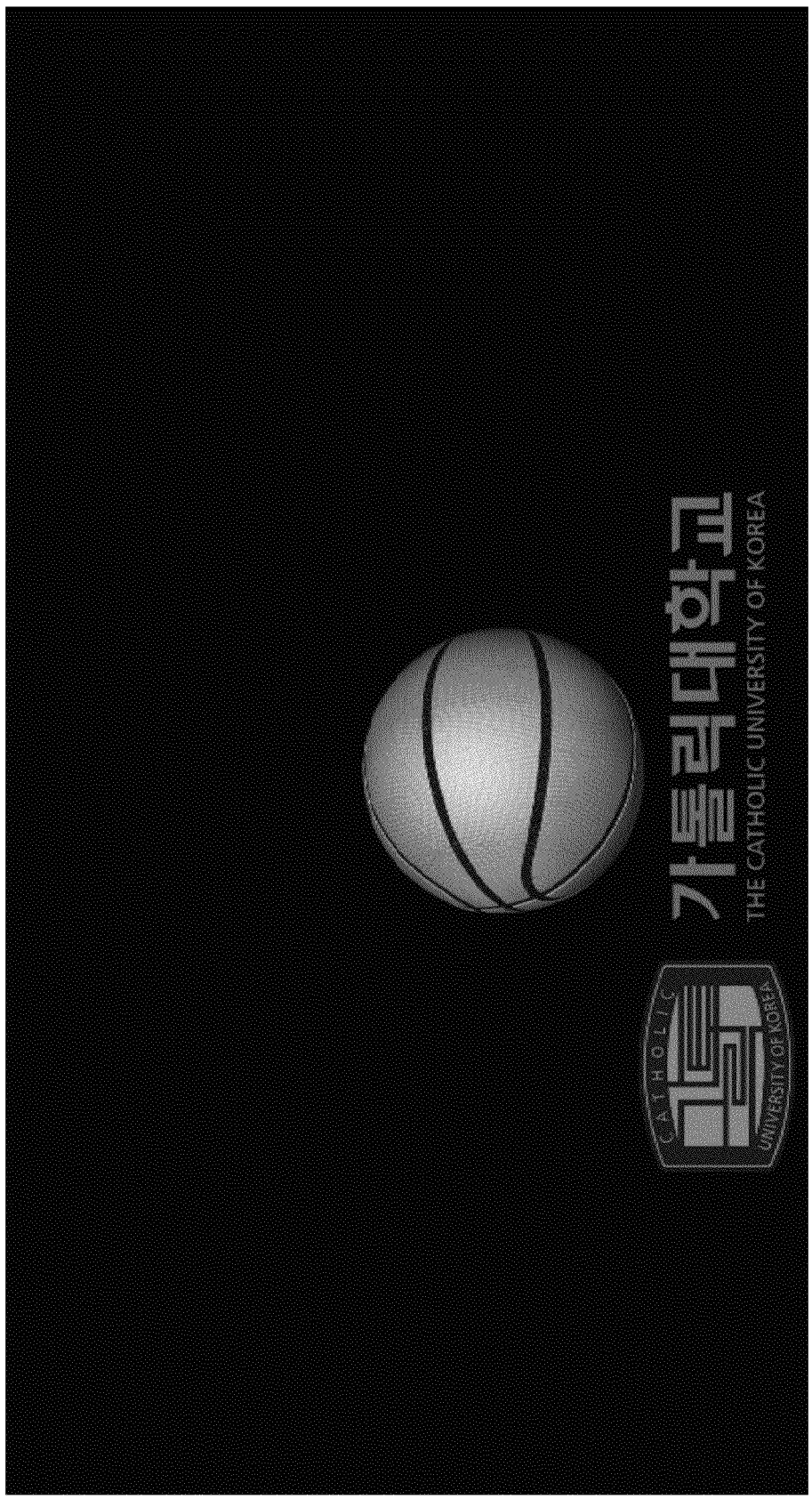
FIGS. 7 to 9 represent examples of 3D image and/or 2D image displayed by a stereovision optometry apparatus according to the invention.
Figure 8:
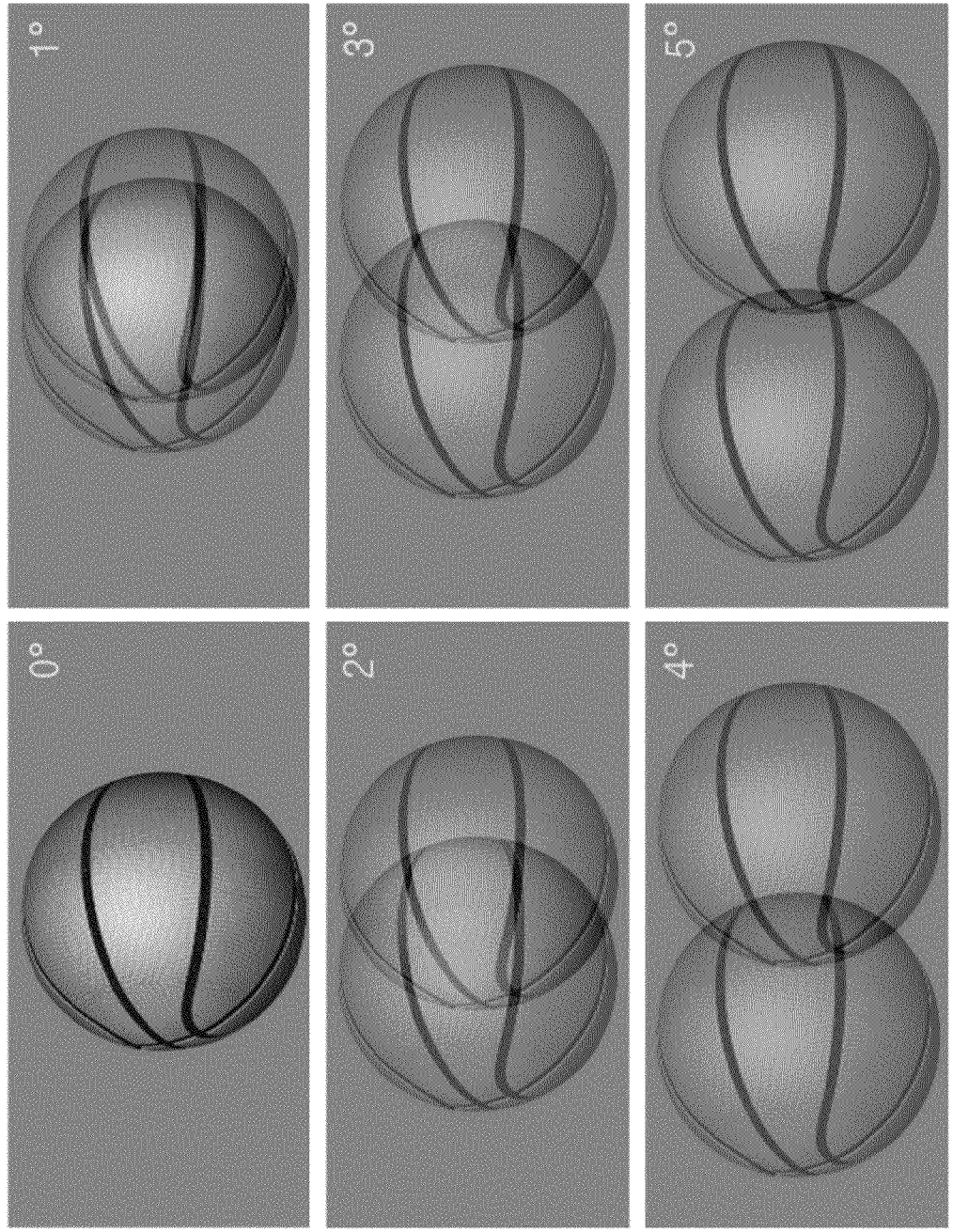

FIG. 7 shows an example of the reference 2D image. FIG. 8 representing examples of the 3D image shows the difference between the left image and the right image according to the protrusion angle when the image is recognized as a 2D image. FIG. 8 explains examples according to the variation of the protrusion angle and the protrusion angle in FIG. 8 varies according to the upward and/or downward movement of the reflective mirror 150.

Figure 9:
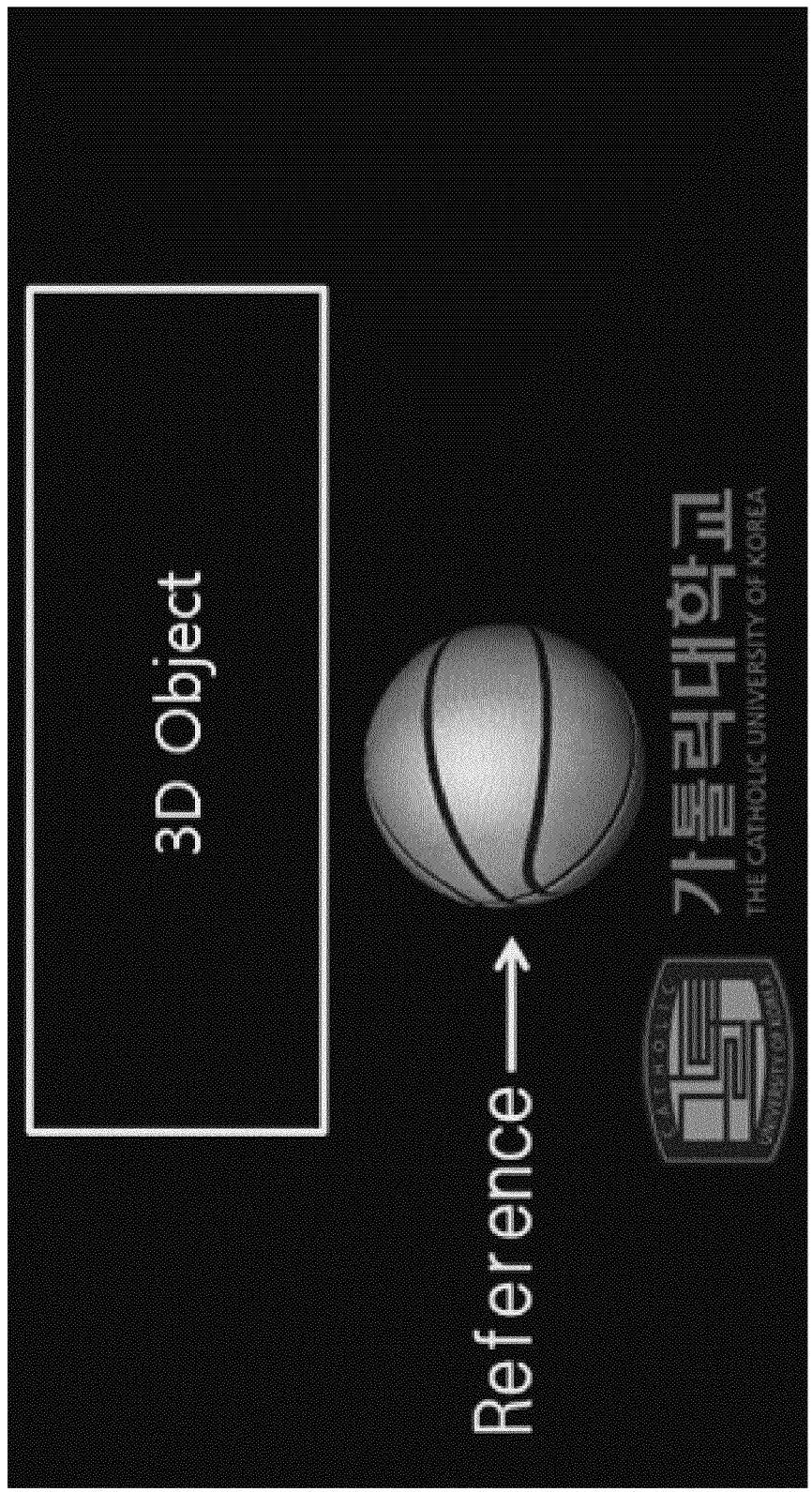

Meanwhile, the placement of the reference 2D image and the 3D image is very important for the accurate measurement. As shown in FIG. 9, the reference 2D image from the reference 2D display unit 120 and the 3D image from the 3D display unit 130 are arranged in such a manner the images are placed vertically on the eyepiece 110.

When the reference 2D image and the 3D image are arranged horizontally, eye's geometric structure with regard to the reference 2D image and the 3D image will be varied significantly. For example, if a viewer focuses on the reference 2D image, the reference 2D image may be often recognized as a 3D image. Therefore, the reference 2D image and the 3D image are arranged vertically on the eyepiece 110.

Referring back to FIG. 1, the stereovision optometry apparatus 100 according to the invention may further comprise a user controller 181 which controls the rotation of the driving motor 161 to move the reflective mirror 150 toward and/or away from the 3D display unit 130 by a user's operation.

Moreover, the stereovision optometry apparatus 100 according to the invention may further comprise an information display 182 which displays stereovision information corresponding to the position of the reflective mirror 150 relative to the 3D display unit.

Therefore, a viewer is able to move the reflective mirror 150 upward and/or downward by the user controller 181 while viewing the images through the eyepiece 110 and also is able to see information as to the degree of his or her own stereovision by the information display 182.

It is intended that the foregoing description has described only a few of the many possible implementations of the present invention, and that variations or modifications of the embodiments apparent to those skilled in the art are embraced within the scope and spirit of the invention.

LIST OF REFERENCE NUMERALS 100 stereovision optometry apparatus
110 eyepiece
120 reference 2D display unit
130 3D display unit
140 half mirror
150 reflective mirror
161 driving motor
162 ball screw
163 ball nut
164 guide bar
170 frame body
181 user controller
182 information screen

I claim:

1. A stereovision optometry apparatus comprising:
   a 3D display unit for displaying a 3D image;
   a reference 2D display unit for displaying a reference 2D image;
   an eyepiece arranged opposite the reference 2D display unit and configured to view the 3D image and the reference 2D image;
   a reflective mirror arranged opposite the 3D display unit and configured to move toward and away from the 3D display unit; and
   a half mirror arranged between the 3D display unit and the reflective mirror and disposed at a point where a propagation path of the reference 2D image and a propagation path of the 3D image intersect;
   wherein the 2D image from the reference 2D display unit penetrates through the half mirror and then reaches the eyepiece; and
   wherein the 3D image from the 3D display unit penetrates the half mirror and then is reflected on the reflective mirror, and the reflected image is reflected on the half mirror and reaches the eyepiece.

2. The apparatus according to claim 1, wherein the half mirror is arranged in such a manner that it has an inclination of 45° with respect to the propagation path of the reference 2D image and the propagation path of the 3D image.

3. The apparatus according to claim 1, further comprising mirror-movement means for moving the reflective mirror toward and away from the 3D display unit along the propagation path of the 3D image.

4. The apparatus according to claim 3, wherein the mirror-movement means comprises:
   a ball screw arranged along the direction of the reflective mirror which moves toward and away from the 3D display unit;
   a ball nut which moves back and forth by the rotation of the ball screw to make the reflective mirror move toward and away from the 3D display unit; and
   a driving motor to rotate the ball screw.

5. The apparatus according to claim 4, wherein the mirror-movement means further comprises at least one guide bar which is arranged along the moving direction of the reflective mirror to guide the reflective mirror toward and away from the 3D display unit.

6. The apparatus according to claim 5, wherein the reflective mirror is provided with a plurality of through-holes into which the ball screw and the guide bar penetrate, and the through-holes are formed on the edges of the reflective mirror.

7. The apparatus according to claim 4, further comprising a user controller which controls the rotation of the driving motor to move the reflective mirror toward and away from the 3D display unit.

8. The apparatus according to claim 4, further comprising an information display which displays stereovision information corresponding to the position of the reflective mirror relative to the 3D display unit.

9. The apparatus according to claim 1, wherein the reflective mirror is arranged to move back and forth between a position closest to the 3D display unit and a position farthest from the 3D display unit; and wherein when the reflective mirror is located closest to the 3D display unit, the reflective mirror is arranged in such a manner that the length of the propagation path of the 3D image from the 3D display unit to the eyepiece is the same as the length of the propagation path of the reference 2D image from the reference 2D display unit to the eyepiece.

10. The apparatus according to claim 1, wherein the reference 2D image from the reference 2D display unit and the 3D image from the 3D display unit are arranged in such a manner the images are placed vertically on the eyepiece.

* * * * *